United States Patent
Raczynski

(10) Patent No.: US 7,953,944 B2
(45) Date of Patent: May 31, 2011

(54) DYNAMIC DATA ARCHIVING WITH DYNAMICALLY DEFINED RULES AND DYNAMICALLY DEFINED PARAMETER

(75) Inventor: Artur Raczynski, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 628 days.

(21) Appl. No.: 11/670,497

(22) Filed: Feb. 2, 2007

(65) Prior Publication Data

US 2008/0189496 A1 Aug. 7, 2008

(51) Int. Cl.
*G06F 13/00* (2006.01)

(52) U.S. Cl. .................. 711/161; 711/154; 711/163

(58) Field of Classification Search .............. 711/154, 711/161, 163
See application file for complete search history.

(56) References Cited

U.S. PATENT DOCUMENTS

| | | | |
|---|---|---|---|
| 6,408,198 B1* | 6/2002 | Hanna et al. | 600/323 |
| 6,574,629 B1* | 6/2003 | Cooke et al. | 1/1 |
| 7,120,644 B1* | 10/2006 | Canessa et al. | 707/102 |
| 7,501,995 B2* | 3/2009 | Morita et al. | 345/7 |
| 2005/0148861 A1* | 7/2005 | Ramanathan et al. | 600/410 |
| 2006/0082809 A1* | 4/2006 | Loukipoudis et al. | 358/1.15 |
| 2006/0114254 A1* | 6/2006 | Day et al. | 345/424 |
| 2006/0167945 A1* | 7/2006 | Trautner | 707/104.1 |
| 2006/0239573 A1* | 10/2006 | Novatzky et al. | 382/239 |
| 2007/0071294 A1* | 3/2007 | Mahesh | 382/128 |
| 2007/0185395 A1* | 8/2007 | Glaser-Seidnitzer et al. | 600/410 |
| 2007/0269117 A1* | 11/2007 | Ernvik et al. | 382/232 |
| 2007/0280560 A1* | 12/2007 | Dennison et al. | 382/305 |
| 2008/0052313 A1* | 2/2008 | Keen | 707/104.1 |
| 2008/0147860 A1* | 6/2008 | Edwards et al. | 709/225 |
| 2009/0164474 A1* | 6/2009 | Noumeir | 707/10 |

* cited by examiner

*Primary Examiner* — Reba I Elmore
(74) *Attorney, Agent, or Firm* — Schiff Hardin LLP

(57) ABSTRACT

A method and apparatus for archiving medical data in one of two or more storage modules, comprising a short time storage module with fast access and a long time storage module with slow access. The method comprises the steps of defining at least one set of rules for executing the method for archiving and defining at least one parameter for controlling the method for archiving; wherein the method depends on the at least one set of rules and/or on the at least one parameter.

19 Claims, 1 Drawing Sheet

DYNAMIC DATA ARCHIVING WITH DYNAMICALLY DEFINED RULES AND DYNAMICALLY DEFINED PARAMETER

CROSS-REFERENCE TO RELATED APPLICATIONS

None.

STATEMENT REGARDING FEDERALLY SPONSORED RESEARCH OR DEVELOPMENT

None.

BACKGROUND OF THE INVENTION

1. Field of the Invention

The present invention relates to an apparatus and a method for archiving medical data in storage modules of different kinds.

2. Brief Description of the Related Art

Over the past years, the volume of medical data that has to be stored and archived in clinical institutions or hospitals has massively increased. In conventional systems, the data stream or the medical data is supported and managed by a picture and archive communication system, also known as "PACS". A PACS can handle and organize data streams from various modalities for medical examination as for example, computer assisted tomographs, mammographic apparatus, endoscopic apparatus, magnetic resonance imaging apparatus, radiographic apparatus, ultrasonographic apparatus, position emission tomographs (PET) and similar.

During a patient examination, for instance, digital data (medical images) taken by a modality are deposited, i.e., saved in a short time storage module of the PACS. The short time storage module of the PACS provides a fast storage medium, and thus a fast access to save and store the data.

Then, a copy of the stored spate of medical images can be transferred from the short time storage module of the PACS to workstation or personal computers of physicians who need such information for further therapies, diagnoses, etc. of the patient. The image data is retransferred to the short time storage module, if the physician has manipulated the image data.

After a period of time, the stored data is then transferred from the short time storage module to a long time storage module of the PACS. The long time storage module often has a slow storage medium (for example a magnetic tape) with slow access possibilities for storing and re-accessing the data. After the transfer of medical data has completed, the data in the short time storage module is deleted after a period of time or if the storage medium of the short time storage module has reached its maximum storage capacity.

With respect to managing the electronic medical data, the use of a PACS known from the prior art within for example, a clinical institution, is not economic, efficient and not optimal. The medical data that has to be stored is not managed dynamically, i.e., there is no configurable and modifiable method of archiving and storing medical data according to which, for example, properties of the medical data determine the further process of storage, access or the examination as such in dependence of configurable rules and/or parameters.

For example, if the level of a specific storage volume, i.e., the maximum storage capacity of the short time storage module is reached, then sets of stored data that are older than a predefined number of days, are deleted from the short time storage module. However, the needs of clients show that some medical data can be deleted earlier from the expensive, useful and limited short time storage module, because the medical data depends on several characteristics or parameters such as modality, clinical picture of the patient, physician, etc. The medical data does not comprise any parameter that controls the further handling and storing of the data. There is also no known possibility to assign such a parameter to medical data, for example, to a medical image file.

Presently, all instances of digital medical image data are rigidly archived according to a static archiving concept. For example, images are archived in the long time storage module for N years until they are deleted. However, it is not necessary that all medical data is stored and archived for N years. The time spans for which medical data are archived, differ. Some types of images need to be stored longer than others, depending on various factors. Consequently, medical data should be stored, for example, in dependence on its medical importance, its modality, etc. Unfortunately, in present systems, this high degree of configurability of the archiving concept, as mentioned above, has not been implemented.

A further problem is to be seen in the large amount of medical data that is produced by the medical modalities, because the storage capacity of both the short time storage modules and the long time storage modules are limited. The access to medical data stored in the long time storage module with slow access is often time-consuming and cumbersome.

Consequently, there it would be helpful to provide an improved method and apparatus for archiving and/or storing and accessing medical data in the storage modules of different kind.

SUMMARY OF THE INVENTION

According to the present invention, a method for archiving data in at least one of at least two storage modules is provided. The data is associated with at least one medical examination. A first one of the at least two storage modules comprises at least one short time storage module. A second one of the at least two storage modules comprises at least one long time storage module. The at least one long time storage module has at least one long time storage sub module with a fast access and the at least one long time storage module has at least one long time storage sub module with a slow access. The method for archiving data comprises:

Defining at least one set of rules for executing the method for archiving,

Defining at least one parameter for controlling the method for archiving, wherein the method depends on the at least one set of rules and/or on the at least one parameter.

The data that has to be archived may be, generated from a modality such as computer assisted tomograph, a mammographic apparatus, a endoscopic apparatus, a magnetic resonance imaging apparatus, or a radiographic apparatus or a ultrasonographic apparatus position emission tomographs or any other medical apparatus for generating medical data within a medical examination of a patient.

The short time storage module can be, for example, a RAID system and can comprise several fast hard disc drives. Originally, RAID means redundant array of inexpensive disks, but now, RAID is known as redundant array of independent disks. The multiple hard disk drives of the RAID system share or replicate data among the drives in order to increase the data integrity and the speed of access to the data. The hard disc drives can store the medical data and can provide fast access to the stored medical data. Alternatively, the short time storage module can also be an optical memory, a flash memory such as a USB memory stick or any other type of memory that can provide fast access. The term "fast access short time storage module" used in this description relates to a short time storage module with a fast access.

The long time storage sub module with a fast access may be, a RAID system and can comprise several fast hard disc drives. The hard disc drives may store the medical data and can provide fast access to the medical data, stored. Alternatively, the long time storage sub module with a fast access can also be an optical memory, a flash memory such as a USB memory stick or any other type of memory that can provide fast access. The long time storage sub module with a slow access can be, for example, a magnetic tape drive or a streamer. Such a storage module is low priced and robust. The term "fast access long time storage sub module" used in this description relates to a long time storage sub module with a fast access. The term "slow access long time storage sub module" used in this description relates to a long time storage sub module with a slow access.

It has to be mentioned that the fast access long time storage sub module and the slow access long time storage sub module could be two separate storage modules or, alternatively, could be integrated in one module. Further, also the other storage modules of the invention can be provided as separate modules or as a combination of sub modules, integrated in one module.

Preferably, a first copy of the medical data is stored in the short time storage module (STS). A second copy is stored in the fast access long time storage sub module and a third copy is stored in the slow access long time storage sub module, provided that the at least one rule or at least one parameter requires to do so.

In another setting, it can be defined that there will be no copying. If so, the data are only transferred from a first storage to a second one. After completing the transfer, the data are no longer saved in the first storage, which helps to reduce storage capacity.

The provision of a long time storage sub module with a fast access allows, for example, the execution of comparative tests. Within the procedure of a comparative test, new medical data (e.g. x-ray-genograms, radiographic images, etc.) is compared with elder medical data by a physician. The access to the elder medical data stored on the long time storage sub module with slow access is very time-consuming. According to the invention and the method provided for comparative tests between medical images from the fast access short time storage module where a copy of the new medical data is stored and the fast long time storage sub module can be realized very easily and are not time consuming.

The method according to the invention provides a better handling and managing of medical data and copies of the medical data, for example, in a communications network, in a PACS, etc. The method can be, for example, used within a clinical institution such as a hospital or in a doctor's surgery or between the hospital and the doctor's surgery, if the physician needs access to medical data stored in a PACS of a hospital.

The data can be information according to the DICOM standard. DICOM implies digital imaging and communications in medicine and is a well known standard for handling, storing and managing of medical image data. The medical image data comprises a file format definition and a network communications protocol.

The defining of the at least one set of rules and/or the defining of the at least one parameter can control and determine the storage duration of the medical data or copies of the medical data, for example, medical images in the fast access long time storage sub module and/or in the slow access long time storage sub module and/or in the fast short time storage sub module. For example, one of the at least one set of rules can be applied for executing the method for archiving such that a copy of the medical data is stored in the short time storage module and the fast access long time storage sub module for a specified period of time. The period of time can be specified by one or more parameters of the at least one parameter in dependence of the modality or of the category of the medical data or of the importance of the medical data, etc. According to another aspect of the invention, this set (or list) of dependency parameters may vary and may be set adaptively according to the present archiving case. Further, the archiving and/or storage concept may be defined by the user and/or may be defined dynamically.

According to the present invention the archiving concept is based on rules and/or parameters, which generally provide(s) for a higher degree of configurability. For example the archiving concept, particularly the archiving period, depends on several factors, like modality, disease pattern, organ, legal background, technological resources etc.

The at least one parameter can represent individual characteristics of the patient. In another aspect of the invention, the at least one parameter can represent kind of medical examination. The at least one set of rules executes the method for archiving using the at least one parameter. The at least one parameter can be a dynamically defined parameter. The at least one rule can be a dynamically defined rule. In another aspect of the invention, the at least one parameter can be defined by a modality or a physician or the like. In another aspect of the invention, the at least one rule can be based on a modality or a physician or the like. The at least one rule and/or the at least one set of rules can be defined by an external administration via a telecommunications network such as the Internet, intranet, etc. According to another aspect of the invention, the at least one rule and/or the at least one set of rules may be predefined.

According to another aspect of the invention, archiving is based on both the at least one set of rules and the at least one parameter.

Archiving can be based solely on the at least one set of rules or on the at least one parameter or solely on one parameter.

The method for archiving data, wherein the data is associated with a patient or a medical examination, the method comprising, for example:
 storing at least one portion of medical data in a short time storage module for a first period of time;
 defining a first parameter for the at least one portion of medical data indicating whether the at least one portion of medical data is used at a later point in time after the first period of time expired;
 transferring the at least one portion of medical data in a slow access long time storage sub module when the first period of time expires; and
 copying the at least one portion of medical data in a fast access long time storage module when the first parameter indicates that said at least one portion of medical data is used at a later point in time.

The method according to the invention can, for example, provide rules and parameters for executing and controlling a storage duration of medical data in different kinds of storage modules and the method can, for example, provide rules and parameters for determining the access and/or the type of storage module. This allows, for example, that the method for archiving is adaptable to various different storage conditions.

In accordance with another aspect of the invention, the method for archiving data can comprise copying the data in dependence of the at least one set of rules and in dependence of the at least one parameter.

One parameter of the at least one parameter can determine, for example, a storage duration of the medical data in the short time storage module. Another parameter of the at least one parameter can determine, for example, a storage duration of the medical data in the long time storage module. Still another parameter of the at least one parameter can determine, for example, an assignment to the medical data for either storing the medical data in the slow access long time storage sub module or for storing the medical data in the fast access long time storage sub module.

A rule of the at least one set of rules can be dynamically specified such that it executes the method for archiving according to which it copies medical data with the parameters to the fast access long time storage sub module and determines the storage duration of the copied medical data at, for example, five years. Another rule, for example, can control the method for archiving according to which the medical data is split in several data segments or portions of data, respectively. Then, the portions of the medical data may be distributed and copied at different locations or storage modules according to the rule(s).

The method for archiving data can comprise storing the data in dependence of the at least one set of rules and in dependence of the at least one parameter. The method for archiving data may comprise storing the data in dependence of the at least one set of rules or in dependence of the at least one parameter.

For example, storing the data can be realized dynamically. If there is a bottleneck and the data capacity of the communication network that connects several types of different storage modules is limited, the medical data can be buffered at a specified storage module such as a RAM, SDRAM module and then stored in its designated storage module. Or according to one aspect of the invention there could be defined a rule, stating that the data should not be stored preliminarily, but should solely be archived in an archiving memory for long time storage. Or, another rule could be set, according to which the time limit for storing the data is limited.

At least a portion of the medical data may be stored in the fast access long time storage sub module for a specified period of time. The period of time may be defined by a parameter that is associated with the portion of the medical data. According to another aspect of the invention, the at least one set of rules and/or the at least one parameter may be predefined or might be set by an operator. This allows, for example, that the storing and archiving process may be used for different applications and could be dynamically adapted either automatically or by an operator.

According to another aspect of the invention, the method for archiving data may comprise accessing the data in dependence of the at least one set of rules and in dependence of the at least one parameter.

For example, accessing can comprise accessing at least a portion of stored medical data (e.g. one medical image), wherein the medical data can be stored in the fast access long time storage sub module. Accessing the data can comprise accessing to several portions of one medical data set that is distributed in storage modules of different kind. The accessing can be dynamical, depending on an user interaction, or can be based on an apparatus or on a modality. This allows, for example, that the method for archiving is more flexible.

The method for archiving data can comprise transferring the data in dependence of the at least one set of rules and in dependence of the at least one parameter. Preferably, transferring data from position A to position B means that the data are no longer existent at A, after having completed the transfer process. In this case, the data are not stored twice or manifold.

The medical data can be, for example, transferred from a electronic data processing apparatus of a clinical modality, as described above, to the short time storage module and to the slow access long time storage sub module at the same time via a predefined (data) transfer protocol. The transfer protocol may be a rule of the at least one set of rules for executing the method for archiving. The transferring and/or the transfer protocol can depend on at least one parameter. If the medical data is of great importance, one parameter that is associated with the medical data of great importance may determine a transfer protocol that allows fast communication speeds.

According to another aspect of the invention, the method for archiving data may comprise deleting the data in dependence of the at least one set of rules and/or in dependence of the at least one parameter.

The stored data can, for example, be deleted from the short time storage module after a period of time. The period of time can be dynamically specified by a parameter. According to another aspect of the invention, the period of time can be automatically specified by a parameter. This allows, for example, the saving of costs and administrative efforts for managing the short time storage module.

The method for archiving data that is associated with at least one medical examination may further comprise compressing the data in dependence of the at least one set of rules and/or in dependence of the at least one parameter.

The method for archiving data may further comprise encrypting the data in dependence of the at least one set of rules and/or in dependence of the at least one parameter. The encrypting can be, for example, at least for a transfer time and/or for the storage time. Particularly, a rule might be defined, according to which personal data have to be stored solely in encrypted format.

The method for archiving data may further comprise decrypting the data in dependence of the at least one set of rules and/or in dependence of the at least one parameter.

The method for archiving data may further comprise a defragmentation process or defragmentation at least one of the at least two storage modules in dependence of the at least one set of rules and/or in dependence of the at least one parameter.

The method for archiving data may further comprise searching the data or at least a portion of the data in dependence of the at least one set of rules and in dependence of the at least one parameter. This allows, for example, a faster access with respect to specific data items or data partitions.

The method for archiving data may further comprise checking the data or at least a portion of the data in dependence of the at least one set of rules and in dependence of the at least one parameter. This aspect of the invention provides, for example, for consistency of the data.

The at least one set of rules can comprise at least one rule for determining a number of copies of the data.

The at least one set of rules can be specified automatically or in dependence of a modality or in dependence of a user action. The at least one rule for determining a number of copies of the data or a portion of the data can comprise, for example, copying the stored data or a portion of the stored data from the short time storage module to the long time storage module with a slow access and in dependence of a parameter or copying the stored data or a portion of the stored data from the short time storage module to the long time storage module with a fast access. The stored data or a portion of the stored data can comprise at least one parameter for controlling the method for archiving.

The at least one set of rules may comprise at least one rule for determining at least one of the least two storage modules.

The at least one set of rules can comprise, for example, determining the fast storage module if the data that has to be archived is of great importance or will be used for further applications such as comparative tests/examinations. Otherwise, if the data was potentially of minor importance, it could be configured to be stored on a slow, i.e. long time storage module.

The at least one set of rules can comprise at least one rule for redefining at least one of the least one parameter.

The at least one set of rules can comprise, for example, redefining a parameter of controlling the method for archiving such that a modified value of the parameter is allocated to the parameter, wherein the parameter controls the specified period of time of the data, stored until it is deleted.

The at least one parameter may comprise at least one storage duration parameter for determining a storage duration of the data.

The storage duration parameter may be, for example, different for the same set of data, portion of data or data that is stored in several different storage devices, i.e. storage modules of different kind. This aspect of the invention allows, for example, more flexibility in handling and managing of the data, archived as well as more flexibility of the storage modules.

The at least one storage duration parameter can determine at least one of the at least two storage modules.

The at least one parameter may comprise at least one modality parameter. The at least one modality parameter can be associated with at least one modality, like computer assisted tomographs, mammographic apparatuses, etc. The at least one modality can generate the data via a picture recording device. In practice, different modalities may have different storage conditions. Such a modality can be represented with this parameter.

The at least one parameter can comprise at least one access selection parameter. The at least one access selection parameter can be associated with at least one of the at least two storage modules. For example, a user can determine a storage module with either a fast or a slow access or both.

The at least one parameter may comprise at least one patient related parameter. The at least one patient related parameter can be associated with at least one characteristic of a patient or the at least one patient related parameter can be associated at least an object of investigation of the patient. According to another aspect of the invention, the patient related parameter can be associated with the actuality of a patient examination. Then, a present examination generally would be of major importance, whereas an older patient examination, long time ago, would be of minor importance and therefore could be stored in a storage module with slow access.

According to another aspect of the invention, the fast access can comprise an online access.

The online access can be, for example, access to stored data in a short time storage module via a telecommunications network such as Internet, intranet or any other kind of network.

The data can comprise a file format according to the DICOM standard.

The invention also provides an apparatus for archiving data. The data are associated with at least one medical modality. The apparatus comprises:

at least two storage modules, wherein a first one of the at least two storage modules has at least one short time storage module,
wherein a second one of the at least two storage modules has at least one long time storage module,
the at least one long time storage module having at least one long time storage sub module with a fast access and at least one long time storage sub module with a slow access;
at least one rule definition and execution module for executing the archiving of the data,
at least one parameter definition module for controlling the archiving of the data,
wherein the apparatus is controlled by at least one rule signal from the at least one rule definition and execution module and/or wherein the apparatus is
further controlled by at least one parameter signal from the at least one parameter definition module.

The least one long time storage sub module with the fast access can comprise at least one hard disc drive. This allows a fast access to the data.

The apparatus for archiving data can comprise at least one data access module for accessing the data in dependence of at least one rule signal from the at least one rule definition and execution module and in dependence of at least one parameter signal from the at least one parameter definition module. The apparatus is controlled in dependence of a first (rule) signal and in dependence of a second (parameter) signal. Also, it could be controlled by the first or second signal, solely.

The invention also provides a medical modality for generating data. The medical modality comprises an apparatus for archiving data. The data or at least a portion of the data is associated with the medical modality. The apparatus comprises at least two storage modules, wherein a first one of the at least two storage modules has at least one short time storage module,
wherein a second one of the at least two storage modules has at least one long time storage module,
the at least one long time storage module has at least one long time storage sub module with a fast access and at least one long time storage sub module with a slow access;
at least one rule definition and execution module for executing the archiving of the data;
at least one parameter definition module for controlling the archiving of the data;
wherein the apparatus is controlled by at least one rule signal from the at least one rule definition and execution module and/or
further is controlled by at least one parameter signal from the at least one parameter definition module.

The medical modality can be selected from a group of computer assisted tomographs, mammographic apparatuses, endoscopic apparatuses, magnetic resonance imaging apparatuses, radiographic apparatuses, ultrasonographic apparatuses, position emission tomographs or any other medical apparatus for generating data and combinations thereof.

The invention also provides a computer program product. The computer program product is loadable into at least one memory of a computer readable tangible medium or into an electronic data processing apparatus. The computer program product comprises program code means to perform the method for archiving data in at least one of at least two storage modules. The data is associated with at least one medical examination or study. A first one of the at least two storage modules comprises at least one short time storage module. A second one of the at least two storage modules comprises at least one long time storage module. The at least one long time storage module has at least one long time storage sub module with a fast access and at least one long time storage sub module with a slow access. The method comprises:

defining at least one set of rules for executing the method for archiving;

defining at least one parameter for controlling the method for archiving;

wherein the method depends on the at least one set of rules and/or on the at least one parameter, if the program code means are executed on the computer readable tangible medium or on the electronic data processing apparatus.

According to another aspect of the invention, a computer readable tangible medium is provided. The computer tangible readable medium stores instructions for implementing a process driven by a computer. The instructions control the computer to perform the method for archiving data in at least one of at least two storage modules. The data is associated with at least one medical examination. A first one of the at least two storage modules comprises at least one short time storage module. A second one of the at least two storage modules comprises at least one long time storage module. The at least one long time storage module has at least one long time storage sub module with a fast access and at least one long time storage sub module with a slow access. The method comprises:

defining at least one set of rules for executing the method for archiving;

defining at least one parameter for controlling the method for archiving;

wherein the method depends on the at least one set of rules and/or on the at least one parameter, if the program code means are executed on the computer readable tangible medium or on the electronic data processing apparatus.

The computer readable tangible medium can be a floppy disk, CD-ROM, DVD, hard disk, USB memory stick, etc.

The method can be, for example, implemented on a real time electronic data processing system. The electronic data processing system comprises at least one rule definition and execution module and at least one parameter definition module.

The invention allows, for example, cost saving for the short time storage module without any risk for the patient. The short time storage module may only store the medical data of great importance. The medical data of minor importance is archived in the long time storage module. Consequently, this leads to more storage space, being available of the short time storage module.

The defining of rules and parameters allows, for example, that some sets of medical data (e.g. medical images) can be deleted or removed from the short time storage module at an earlier point of time. The data can be stored a individually specified period of time in the long time storage module according to their importance. This leads to a shorter duration of migration, for example, if the storage technology changes.

The introduction of a limited fast access long time storage sub module allows, for example, a fast access to specified medical data. This leads to a saving of time, because the data and the storage of the data is managed selectively.

According to one aspect of the invention, the content, i.e. the stored data in the short time storage module can be adjusted to clinical needs to minimize, for example, a required storage capacity and to have access to a further fast storage module, namely the fast access long time storage sub module.

The parameters and/or rules for the method of archiving can be, for example, set according to clinic-based criteria, legal criteria, etc.

According to another aspect of the invention, the time for defining the at least one set of rules and/or the at least on parameter may vary. The parameter can be predefined or might be set during the examination. Further, the parameter may be user-based, instance-based or may be determined automatically.

The at least one set of rules and/or the at least one parameter can be defined via an online access. The step of defining the set of rules and the step of defining the parameter optionally could be executed in a different order (firstly parameter, secondly rules), or other steps could be imposed between the two. Further, there could be defined more than one set of rules and more than one parameter.

Still other aspects, features, and advantages of the present invention are readily apparent from the following detailed description, simply by illustrating preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

DESCRIPTION OF THE DRAWINGS

For a more complete understanding of the present invention and the advantages thereof, reference is now made to the following description and the accompanying drawings, in which.

DETAILED DESCRIPTION

Figure 1:
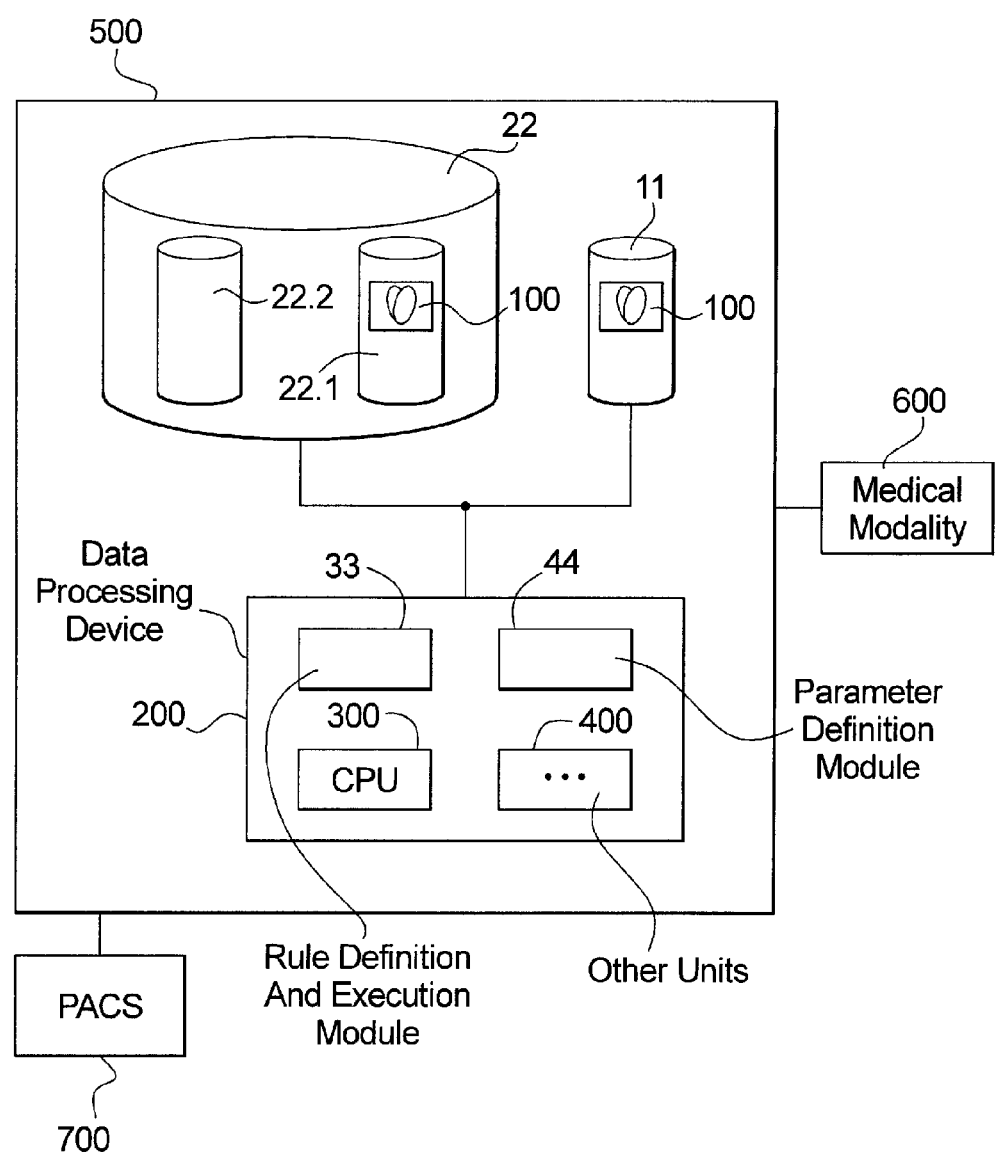
FIG. 1 is a schematic overview of an example of the apparatus according to the invention.

FIG. 1 shows a two-dimensional schematic overview of an example of the apparatus 500 according to the invention. The apparatus 500 comprises a short time storage module 11 with a fast storage medium, and thus with a fast data access for accessing data that is or will be transferred and stored. The short time storage module 11 can be, for example, a RAID system including a plurality of fast hard disc drives 100. The apparatus 500 further comprises a long time storage module 22. The long time storage module 22 has a long time storage sub module 22.1 with a fast medium, and thus with a fast access, and the long time storage module 22 has a long time storage sub module 22.2 with a slow medium, and thus with a slow access to the data. The long time storage sub module 22.2 with the fast access is also termed "fast long time sub module 22.1". The long time storage sub module 22.2 with the slow access is termed "slow long time storage sub module 22.2".

The fast long time storage sub module 22.1 has a RAID system with a plurality of fast hard disc drives 100. The slow long time storage sub module 22.2 has at least one streamer or tape deck, respectively.

The apparatus 500 further comprises a rule definition and execution module 33. In the example of FIG. 1, the rule definition and execution module 33 is part of an electronic data processing device 200. The rule definition and execution module 33 may be a hardware device. The rule definition and execution module 33 may be implemented as software or in hardware and software. According to another aspect of the invention, the rule definition and execution module 33 can also be part of a medical modality 600.

The apparatus 500 further comprises a parameter definition module 44. In the example of FIG. 1, the parameter definition module 44 is part of the electronic data processing device 200. The parameter definition module 44 can be part of a medical modality 600. The parameter definition module 44 can be also provided as a separate module with network access to the other modules.

The electronic data processing device 200 can be of personal or workstation computer type, comprising, for example, a main board, data and network interfaces, a central processing unit (CPU) 300, memory means such as ROM/RAM, communication ports, disk controllers, CD-ROM/DVD/floppy-drives, hard drives, bus systems, a display device, etc. shown as other units at 400.

The apparatus 500 is connected to a medical modality 600. The medical modality 600 may be a computer assisted tomograph, mammographic apparatus, endoscopic apparatus, magnetic resonance imaging apparatus, radiographic apparatus, ultrasonographic apparatus, position emission tomograph or any other medical apparatus for generating data. The data can be medical data and comprise, for example, medical images such as X-ray pictures of a broken leg. Also, other data (besides images, like for example, personal data, header data with respect to an image, modality parameters and other data) could be subject of the method according to the invention.

The parameter definition module 44 contains an arbitrarily configurable chart of parameters. The parameters may represent an archiving concept of, for example, the PACS user of a hospital. To set the values for the parameters an editor in combination with a data input device, such as a keyboard, and a display device can be used. The parameters may, for example, represent needs of physicians, patients, other hospitals, medical modalities, the importance of the corresponding data, etc.

The rule definition and execution module 33 can interpret the parameters or the values of the parameters. The rule definition and execution module 33 can delete medical data from the short time storage module and/or the fast and/or the slow access long time storage sub module according to the defined parameters and/or rules. The medical data can comprise images, spates of images or studies or associated data, like meta data, etc.

Further, the rule definition and execution module 33 can copy the medical data to the fast access long time storage sub module in accordance to the specified parameters. There may also be a signal exchange between the parameter definition module 44 and the rule definition and execution module 33 and the storage modules 11, 22 and the medical modality 600 and other modules, etc. However, this aspect is apparent for the person skilled in the art.

The apparatus 500 of FIG. 1 is connected to a PACS system or a PACS server indicated at 700. In another aspect of the invention, the apparatus 500 can be part of the PACS system, e.g. integrated within the PACS system. In a further aspect, the rule definition and execution module 33 and/or the parameter definition module 44 may be connected to a PACS system by themselves and/or be part of a PACS system. The same aspect may also be relevant for the storage modules 11, 22.

The invention has been described in terms of single preferred examples. A person skilled in the art will recognize that the invention can be practiced with modification within the spirit and scope of the attached claims.

At least, it should be noted that the invention is not limited to the detailed description of the invention and/or the examples of the invention. It is apparent for a person skilled in the art that the invention can be realized at least partially in hardware and/or software and can be transferred to several physical devices or products. The invention can be transferred to at least one computer program product. Further, the invention may be realized with several devices.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A method for archiving medical data in at least one of a plurality of storage modules, the data being associated with at least one medical examination, a first of said plurality of storage modules comprising a short time storage module, a second of said plurality of storage modules comprising a long time storage module, said long time storage module having a fast access long time storage sub module and a slow access long time storage sub module, the method comprising the steps of:

defining a set of rules which are capable of being defined dynamically for dynamically executing the method for archiving, said set of rules being automatically set according to a real time data capacity of a communication network associated with said short time and long time storage modules and a data capacity of said storage modules and sub modules;

defining at least one parameter which is capable of being defined dynamically;

also controlling the method for archiving dynamically by means of the parameter, said parameter being selected from the group consisting of patient-related, examination-related, and a property of the medical data;

storing a first copy of the medical data in the short time storage module, storing a second copy in the fast access long time storage sub module, and storing a third copy in the slow access long time storage sub module, provided that at least one defined rule of said set of rules or said at least one defined parameter requires storage of said medical data;

further controlling the method for archiving dynamically with at least one of said set of rules and said parameter defining a storage duration scheduling wherein a storage duration of the medical data in at least one of said storage modules or sub modules is controlled by at least one of the factors selected from the group consisting of medical modality, disease pattern, organ-related factors, patient-related factors, medical legal background, and medical technological resources; and deleting data in at least one of said storage modules and sub modules in dependence on at least one of said defined set of rules and at least one defined parameter.

2. The method according to claim 1, further comprising the step of:

copying the data in dependence on the defined set of rules and on the defined parameter.

3. The method according to claim 1, further comprising the step of:
    transferring the data in dependence on the defined set of rules and in independence on the defined parameter.

4. The method according to claim 1, wherein the defined set of rules comprises a rule for determining a number of copies of the data.

5. The method according to claim 1, wherein the defined set of rules comprises a rule for determining at least one of the plurality of storage modules.

6. The method according to claim 1, wherein the defined set of rules comprises a rule for redefining the defined parameter.

7. The method according to claim 1, wherein the defined parameter comprises a modality parameter being associated with a modality generating the data.

8. The method according to claim 1 wherein the defined parameter comprises an access selection parameter being associated with at least one of the plurality of storage modules.

9. The method according to claim 1, wherein the defined parameter comprises a patient related parameter being associated with a characteristic of a patient or an object of investigation of the patient.

10. The method according to claim 1, wherein the fast access comprises an online access.

11. The method according to claim 1, wherein the data comprises a file format according to the DICOM standard.

12. The method according to claim 1, further comprising the step of:
    storing the data in dependence on the defined set of rules and in dependence on the defined parameter.

13. The method according to claim 12, further comprising the step of:
    accessing the data in dependence on the defined set of rules and in dependence on the defined parameter.

14. An apparatus for archiving medical data, the data being associated with at least one medical examination, comprising:
    a first storage module comprising a short time storage module;
    a second storage module comprising a long time storage module;
    said long time storage module comprising a fast access long time storage sub module and a slow access long time storage sub module;
    a rule definition and execution module for executing said archiving of medical data in said short time storage module or said long time storage fast access sub module or slow access sub module, said rule definition and execution module defining a set of rules which are capable of being defined dynamically for dynamically executing the archiving, said set of rules being automatically set according to a real time data capacity of a communication network associated with said short time and long time storage modules and a data capacity of said storage modules and sub modules;
    a parameter definition module for controlling said archiving of medical data in said short time storage module or said long time storage fast access sub module or slow access sub module, and said parameter definition module defining at least one parameter which is capable of being defined dynamically for dynamically controlling the archiving, the parameter being selected from the group consisting of patient-related, examination-related, and a property of the medical data;
    a first copy of the medical data being stored in the short time storage module, a second copy being stored in the fast access long time storage sub module, and a third copy being stored in the slow access long time storage sub module, provided that at least one defined rule of said set of rules or said at least one defined parameter requires storage of said medical data; and
    at least one of said rule definition execution module and said parameter definition module further controlling the archiving dynamically with at least one of said set of rules and said parameter defining a storage duration scheduling wherein a storage duration of the medical data in at least one of said storage modules or sub modules is controlled by at least one of the factors selected from the group consisting of medical modality, disease pattern, organ-related factors, patient-related factors, medical legal background, and medical technological resources, and deleting data in at least one of said storage modules and sub modules in dependence on at least one of said defined set of rules and at least one defined parameter.

15. The apparatus for archiving data according to claim 14, wherein said long time storage sub module with fast access comprises at least one hard disc drive.

16. The apparatus for archiving data according to claim 14, further comprising:
    a data access module for accessing data in dependence on a rule signal from the rule definition and execution module and in dependence on a parameter signal from the parameter definition module.

17. A medical modality for generating medical data, the medical modality comprising:
    an apparatus for archiving the medical data, the data being associated with at least one medical examination with the medical modality, the apparatus comprising
    a first storage module comprising a short time storage module;
    a second storage module comprising a long time storage module;
    said long time storage module comprising a fast access long time storage sub module and a slow access long time storage sub module;
    a rule definition and execution module for executing said archiving of data in said short time storage module or said long time storage fast access sub module or slow access sub module, said rule definition and execution module defining a set of rules which are capable of being defined dynamically for dynamically executing the archiving, said set of rules being automatically set according to a real time data capacity of a communication network associated with said short time and long time storage modules and a data capacity of said storage modules and sub modules;
    a parameter definition module for controlling said archiving of medical data in said short time storage module or said long time storage fast access sub module or slow access sub module, and said parameter definition module defining at least one parameter which is capable of being defined dynamically for dynamically controlling the archiving, the parameter being selected from the group consisting of patient-related, examination-related, and a property of the medical data;
    a first copy of the medical data being stored in the short time storage module, a second copy being stored in the fast access long time storage sub module, and a third copy being stored in the slow access long time storage sub module, provided that at least one defined rule of said set of rules or said at least one defined parameter requires storage of said medical data;

at least one of said rule definition execution module and said parameter definition module further controlling the archiving dynamically with at least one of said set of rules and said parameter defining a storage duration scheduling wherein a storage duration of the medical data in at least one of said storage modules or sub modules is controlled by at least one of the factors selected from the group consisting of medical modality, disease pattern, organ-related factors, patient-related factors, medical legal background, and medical technological resources, and deleting data in at least one of said storage modules and sub modules in dependence on at least one of said defined set of rules and at least one defined parameter.

18. The medical modality according to claim 17, wherein the medical modality is selected from the group consisting of a computer assisted tomograph, a mammographic apparatus, an endoscopic apparatus, a magnetic resonance imaging apparatus, a radiographic apparatus, an ultrasonographic apparatus, a position emission tomograph, and any other medical apparatus for generating data and combinations thereof.

19. A computer-readable medium for archiving medical data in at least one of a plurality of storage modules, the data being associated with at least one medical examination, a first of said plurality of storage modules comprising a short time storage module, a second of said plurality of storage modules comprising a long time storage module, the long time storage module having a fast access long time storage sub module and a slow access long time storage sub module, said program performing the steps of:

providing a defined set of rules which are capable of being defined dynamically for dynamically executing the method for archiving, said set of rules being automatically set according to a real time data capacity of a communication network associated with said short time and long time storage modules and a data capacity of said storage modules and sub modules;

providing at least one parameter which is capable of being defined dynamically for also dynamically controlling the method for archiving, the parameter being selected from the group consisting of patient-related, examination-related, and a property of the medical data;

storing a first copy of the medical data in the short time storage module, storing a second copy in the fast access long time storage sub module, and storing a third copy in the slow access long time storage sub module, provided that at least one defined rule of said set of rules or said at least one defined parameter requires storage of said medical data;

further controlling the method for archiving dynamically with at least one of said set of rules and said parameter defining a storage duration scheduling wherein a storage duration of the medical data in at least one of said storage modules or sub modules is controlled by at least one of the factors selected from the group consisting of medical modality, disease pattern, organ-related factors, patient-related factors, medical legal background, and medical technological resources; and deleting data in at least one of said storage modules and sub modules in dependence on at least one of said defined set of rules and at least one defined parameter.

* * * * *